(12) United States Patent
Chapman et al.

(10) Patent No.: US 8,636,706 B2
(45) Date of Patent: Jan. 28, 2014

(54) TRANSFER SETS FOR THERAPY OPTIMIZATION

(71) Applicants: Baxter International Inc., Deerfield, IL (US); Baxter Healthcare S.A., Glattpark (CH)

(72) Inventors: Paul R. Chapman, Lutz, FL (US); Brian J. Connell, Evanston, IL (US); Ying-Cheng Lo, Green Oaks, IL (US)

(73) Assignees: Baxter International Inc., Deerfield, IL (US); Baxter Healthcare S.A., Glattpart (Opfikon) (CH)

( * ) Notice: Subject to any disclaimer, the term of this patent is extended or adjusted under 35 U.S.C. 154(b) by 0 days.

(21) Appl. No.: 13/739,740

(22) Filed: Jan. 11, 2013

(65) Prior Publication Data
US 2013/0131583 A1 May 23, 2013

Related U.S. Application Data

(63) Continuation of application No. 12/696,889, filed on Jan. 29, 2010, now Pat. No. 8,377,012.

(60) Provisional application No. 61/148,680, filed on Jan. 30, 2009.

(51) Int. Cl.
*A61M 5/00* (2006.01)

(52) U.S. Cl.
USPC ............... 604/250; 604/248; 604/30; 604/34

(58) Field of Classification Search
USPC .......... 604/29, 30, 33, 34, 249, 250, 523, 248
See application file for complete search history.

(56) References Cited

U.S. PATENT DOCUMENTS

| 3,447,161 A | 6/1969 | Weikel |
| 3,468,447 A | 9/1969 | Smalley |
| 3,858,580 A | 1/1975 | Ogle |
| 3,986,508 A | 10/1976 | Barrington |

(Continued)

FOREIGN PATENT DOCUMENTS

| CA | 1256343 | 6/1989 |
| DE | 390140 | 2/1924 |

(Continued)

OTHER PUBLICATIONS

Rippe B. et al. Computer Simulation of Peritoneal Fluid Transport in CAPD. Kidney International, vol. 40 (1991), pp. 315-325.

(Continued)

*Primary Examiner* — Laura Bouchelle
(74) *Attorney, Agent, or Firm* — K&L Gates LLP

(57) ABSTRACT

Transfer sets are disclosed in the present patent. The transfer set provides a connection between a source of peritoneal dialysis fluid and a patient for whom peritoneal dialysis has been prescribed. The transfer sets disclosed herein are smaller and provide a more compact and convenient device by which a dialysis patient controls the flow of dialysis fluid to and from the peritoneum of the patient. The devices are more compact and convenient because they include more convenient mechanisms for starting and stopping flow of the dialysis fluid. It is also easy to determine whether the mechanism is in a closed or open configuration by simply looking at the mechanism.

23 Claims, 10 Drawing Sheets

(56) References Cited

U.S. PATENT DOCUMENTS

| | | | |
|---|---|---|---|
| 4,201,208 A | 5/1980 | Cambio, Jr. |
| 4,334,551 A | 6/1982 | Pfister |
| 4,354,490 A | 10/1982 | Rogers |
| 4,432,764 A | 2/1984 | Lopez |
| 4,432,766 A | 2/1984 | Bellotti et al. |
| 4,457,749 A | 7/1984 | Bellotti et al. |
| 4,503,333 A | 3/1985 | Kulin et al. |
| 4,511,359 A | 4/1985 | Vaillancourt |
| 4,526,572 A | 7/1985 | Donnan et al. |
| 4,551,146 A | 11/1985 | Rogers |
| 4,580,816 A | 4/1986 | Campbell et al. |
| 4,610,469 A | 9/1986 | Wolff-Mooij |
| 4,623,327 A | 11/1986 | Mahurkar |
| 4,624,664 A | 11/1986 | Peluso et al. |
| 4,655,762 A | 4/1987 | Rogers |
| 4,675,004 A | 6/1987 | Hadford et al. |
| 4,701,159 A | 10/1987 | Brown et al. |
| 4,770,652 A | 9/1988 | Mahurkar |
| 4,810,241 A | 3/1989 | Rogers |
| 4,816,221 A | 3/1989 | Harvey et al. |
| 4,842,582 A | 6/1989 | Mahurkar |
| 4,895,570 A | 1/1990 | Larkin |
| 4,941,517 A | 7/1990 | Galloway |
| 4,983,161 A | 1/1991 | Dadson et al. |
| 4,985,034 A | 1/1991 | Lipton |
| 5,009,636 A | 4/1991 | Wortley et al. |
| 5,100,394 A | 3/1992 | Dudar et al. |
| 5,137,524 A | 8/1992 | Lynn et al. |
| 5,188,593 A | 2/1993 | Martin |
| 5,190,534 A | 3/1993 | Kendell |
| 5,203,056 A * | 4/1993 | Funk et al. ............... 24/543 |
| 5,211,638 A | 5/1993 | Dudar et al. |
| 5,242,425 A | 9/1993 | White et al. |
| 5,263,930 A | 11/1993 | Ensminger |
| 5,269,764 A | 12/1993 | Vetter et al. |
| 5,279,605 A | 1/1994 | Karrasch et al. |
| 5,324,128 A | 6/1994 | Gueret |
| 5,350,357 A | 9/1994 | Kamen et al. |
| 5,372,147 A | 12/1994 | Lathrop, Jr. et al. |
| 5,378,230 A | 1/1995 | Mahurkar |
| 5,393,101 A | 2/1995 | Matkovich |
| 5,431,280 A | 7/1995 | Bryant |
| 5,437,650 A | 8/1995 | Larkin et al. |
| 5,445,610 A | 8/1995 | Evert |
| 5,456,675 A | 10/1995 | Wolbring et al. |
| 5,489,278 A | 2/1996 | Abrahamson |
| 5,501,676 A | 3/1996 | Niedospial et al. |
| 5,507,733 A | 4/1996 | Larkin et al. |
| 5,555,897 A | 9/1996 | Lathrop, Jr. et al. |
| 5,571,093 A | 11/1996 | Cruz et al. |
| 5,582,600 A | 12/1996 | Loh |
| 5,617,012 A | 4/1997 | Murakami |
| 5,620,427 A | 4/1997 | Werschmidt et al. |
| 5,694,978 A | 12/1997 | Heilmann et al. |
| 5,722,947 A | 3/1998 | Jeppsson et al. |
| 5,743,892 A | 4/1998 | Loh et al. |
| 5,776,116 A | 7/1998 | Lopez et al. |
| 5,782,808 A | 7/1998 | Folden |
| 5,810,398 A | 9/1998 | Matkovich |
| 5,827,238 A | 10/1998 | Kelley |
| 5,827,820 A | 10/1998 | duMoulin et al. |
| 5,843,474 A | 12/1998 | Williams |
| 5,902,336 A | 5/1999 | Mishkin |
| 5,938,634 A | 8/1999 | Packard |
| 6,027,489 A | 2/2000 | Galato |
| 6,074,359 A | 6/2000 | Keshaviah |
| 6,079,432 A | 6/2000 | Paradis |
| 6,096,011 A | 8/2000 | Trombley, III et al. |
| 6,105,770 A | 8/2000 | Vasudeva |
| 6,117,122 A | 9/2000 | Din et al. |
| 6,183,465 B1 | 2/2001 | Meier et al. |
| 6,183,467 B1 | 2/2001 | Shapeton et al. |
| 6,232,286 B1 | 5/2001 | Goodearl et al. |
| 6,234,992 B1 | 5/2001 | Haight et al. |
| 6,311,838 B1 | 11/2001 | Johnson et al. |
| 6,358,241 B1 | 3/2002 | Shapeton et al. |
| 6,367,640 B1 | 4/2002 | Julian |
| 6,497,676 B1 | 12/2002 | Childers et al. |
| 6,558,667 B2 | 5/2003 | Nakanishi |
| 6,585,677 B2 | 7/2003 | Cowan, Jr. et al. |
| 6,585,695 B1 | 7/2003 | Adair et al. |
| 6,592,542 B2 | 7/2003 | Childers et al. |
| 6,595,948 B2 | 7/2003 | Suzuki et al. |
| 6,814,547 B2 | 11/2004 | Childers et al. |
| 6,932,787 B2 | 8/2005 | Cowan et al. |
| 7,107,837 B2 | 9/2006 | Lauman et al. |
| 7,153,286 B2 | 12/2006 | Busby et al. |
| 7,232,419 B2 | 6/2007 | Castellanos |
| 7,297,689 B2 | 11/2007 | Miyata |
| 7,303,541 B2 | 12/2007 | Hamada et al. |
| 7,354,417 B1 | 4/2008 | Levin et al. |
| 7,421,316 B2 | 9/2008 | Gray et al. |
| 7,507,219 B2 | 3/2009 | Noack |
| 7,507,220 B2 | 3/2009 | Childers et al. |
| 7,618,392 B2 | 11/2009 | Martis et al. |
| 2001/0040127 A1 | 11/2001 | Donig et al. |
| 2002/0010437 A1 | 1/2002 | Lopez et al. |
| 2003/0006610 A1 | 1/2003 | Werth |
| 2003/0184090 A1 | 10/2003 | Guala |
| 2004/0087986 A1 | 5/2004 | Ott |
| 2004/0111078 A1 | 6/2004 | Miyahara |
| 2004/0111293 A1 | 6/2004 | Firanek et al. |
| 2004/0111294 A1 | 6/2004 | McNally et al. |
| 2004/0238776 A1 | 12/2004 | Peters et al. |
| 2005/0089994 A1 | 4/2005 | Neftel |
| 2007/0106247 A1 | 5/2007 | Burnett et al. |
| 2008/0097283 A1 | 4/2008 | Plahey |
| 2008/0183126 A1 | 7/2008 | Landherr et al. |
| 2008/0183127 A1 | 7/2008 | Landherr et al. |
| 2008/0243211 A1 | 10/2008 | Cartwright et al. |
| 2009/0076856 A1 | 3/2009 | Darby et al. |
| 2009/0187139 A1 | 7/2009 | Mastalli et al. |
| 2009/0222119 A1 | 9/2009 | Plahey et al. |
| 2009/0271119 A1 | 10/2009 | Hamada et al. |
| 2009/0275881 A1 | 11/2009 | Lo et al. |
| 2009/0275883 A1 | 11/2009 | Chapman et al. |
| 2009/0294339 A1 | 12/2009 | Biewer et al. |
| 2009/0299273 A1 | 12/2009 | Lee et al. |
| 2010/0010428 A1 | 1/2010 | Yu et al. |

FOREIGN PATENT DOCUMENTS

| | | |
|---|---|---|
| EP | 0133020 | 2/1985 |
| EP | 0554722 | 8/1993 |
| EP | 0896827 | 2/1999 |
| EP | 1243280 | 9/2002 |
| EP | 0092528 | 3/2003 |
| EP | 1623731 | 8/2006 |
| EP | 1872814 | 1/2008 |
| GB | 894854 | 4/1962 |
| GB | 927151 | 5/1963 |
| GB | 2067075 | 7/1981 |
| GB | 2343723 | 5/2005 |
| JP | 9192216 | 7/1997 |
| JP | 10248924 | 9/1998 |
| JP | 11057419 | 3/1999 |
| JP | 11128359 | 5/1999 |
| JP | 2000014772 | 1/2000 |
| JP | 200140099 | 5/2000 |
| WO | WO 97/00095 | 1/1997 |
| WO | WO 97/35634 | 10/1997 |
| WO | WO 03/099355 | 12/2003 |
| WO | WO 2008/027967 | 3/2008 |

OTHER PUBLICATIONS

Vonesh E. F. and Rippe B., Net fluid absorption under membrane transport models of peritoneal dialysis, Blood Purif 1992; 10:209-226.

International Search Report, PCT/US2009/042106.

International Search Report, PCT/US2009/042103.

* cited by examiner

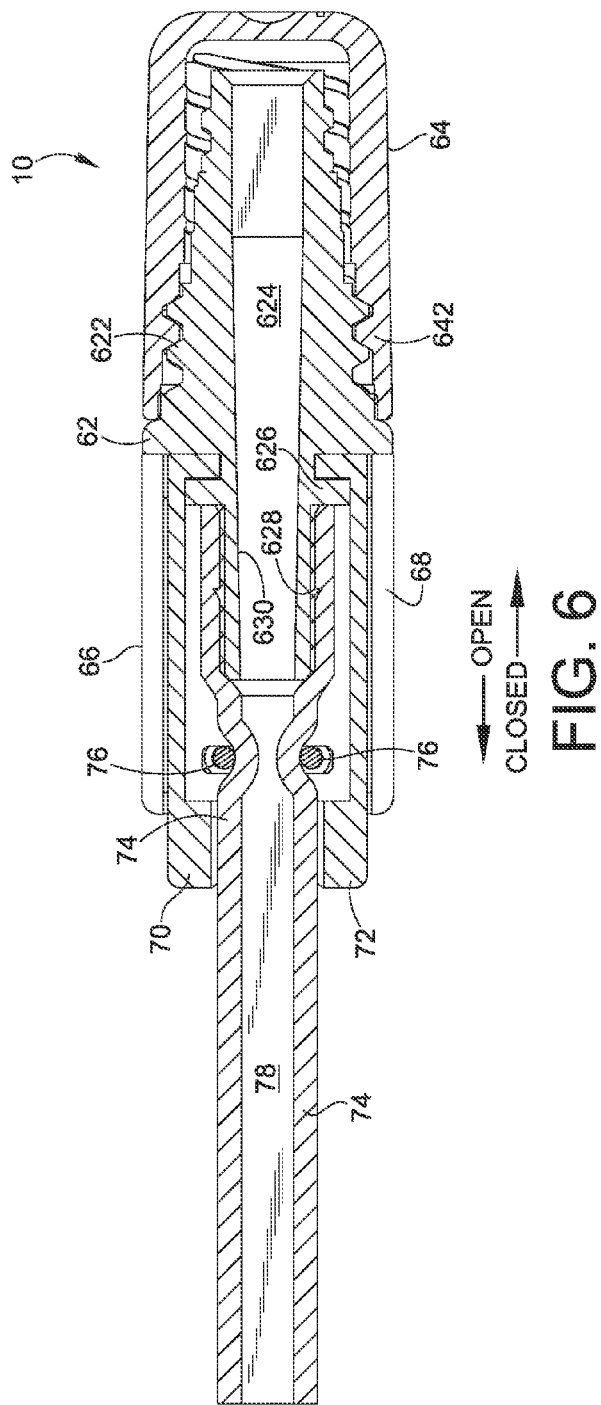
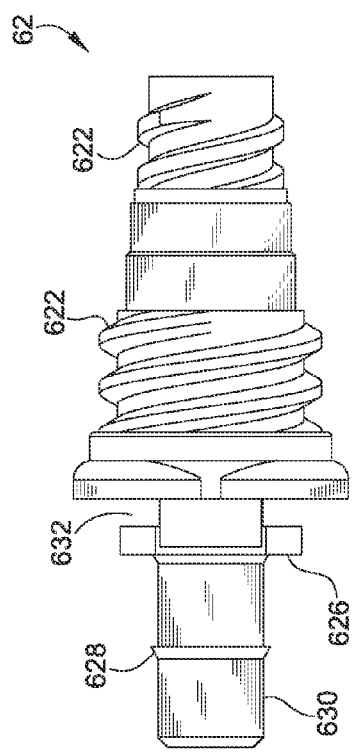
FIG. 6
FIG. 7

TRANSFER SETS FOR THERAPY OPTIMIZATION

PRIORITY CLAIM

This application is a continuation of U.S. patent application Ser. No. 12/696,889, filed on Jan. 29, 2010, which is a non-provisional of U.S. Provisional Patent Application Ser. No. 61/148,680, filed Jan. 30, 2009, the entire contents of each which are expressly incorporated herein by reference.

BACKGROUND

The present disclosure relates generally to medical fluid delivery systems and methods. More particularly, this disclosure includes transfer sets or transfer systems for connecting a source of fluid to a patient for whom the fluid has been prescribed. The transfer sets described typically have a first closed position in which transfer of fluid is not allowed and a second open position in which transfer is allowed. Whether the transfer set is in the first position or the second position can be determined by looking to see whether tubing in the transfer set is occluded or not.

Due to various causes, a person's renal system can fail. Renal failure produces several physiological impairments and difficulties. The balance of water, minerals and the excretion of daily metabolic load is no longer possible and toxic end products of nitrogen metabolism (urea, creatinine, uric acid, and others) can accumulate in blood and tissue. Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Another form of kidney failure treatment involving blood is hemofiltration ("HF"), which is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient between treatments is ultrafiltered over the course of the HF treatment, providing a convective transport mechanism that is particularly beneficial in removing middle and large molecules.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

Peritoneal dialysis machines are used to accomplish this task. Such machines are described, for example, in the following U.S. Patents, all of which are incorporated by reference in their entirety, as though each patent were set forth herein, page by page, in its entirety: U.S. Pat. Nos. 5,350,357; 5,324,422; 5,421,823; 5,431,626; 5,438,510; 5,474,683; 5,628,908; 5,634,896; 5,938,634; 5,989,423; 7,153,286; and 7,208,092.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement. There is room for improvement in the selection of dwell times for each patient.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. These systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

In each of the kidney failure treatment systems discussed above, it is important to control ultrafiltration, which is the process by which water (with electrolytes) moves across a membrane, such as a dialyzer or peritoneal membrane. Each patient is also different in terms of response to dialysis, that is, the amount of water and waste removed in a given time period, using a given fill volume, a particular dialysis fluid, and so forth. Better outcomes may be provided using at least some of the techniques disclosed in U.S. Prov. Appl. 61/050, 144, entitled "Optimizing Therapy Outcomes for Peritoneal Dialysis," filed on May 2, 2008, which is hereby incorporated by reference in its entirety and is relied on.

Part of controlling the flow of peritoneal dialysis lies in occluding and opening the tube or tubes used in providing peritoneal dialysis fluid to the patient or in draining the peritoneal dialysis fluid from the patient. The transfer sets used for occluding and permitting flow tend to be bulky and uncomfortable, especially for patients who receive peritoneal dialysis therapy while reclining in bed. It would be an advance if transfer sets were more compact, smaller and lighter, while still providing positive occluding or opening of the transfer tubing. This is also an advantage for patients using a portable or wearable artificial kidney.

SUMMARY

One embodiment is a transfer system. The transfer system includes a connector having a luer connection on one end and a connection for tubing on an opposite end, and also includes an upper housing and a lower housing adapted to fit around the tubing, the upper and lower housings assembled about a portion of the connector. The transfer system includes first and second occluding pins captured within slots of the upper and lower housings, the first and second occluding pins adapted to occlude and open a lumen of the tubing, and also includes left and right retractors configured about the upper and lower housings, the left and right retractors each having an upper and a lower cam surface for the first and second occluding pins, wherein the tubing is occluded by moving the retractors to a first position in which the first and second occluding pins squeeze and occlude the tubing and wherein the tubing is opened by moving the retractors to a second position in which the first and second occluding pins are refracted, allowing the tubing to open Another embodiment is a transfer system. The transfer system includes a connector having a luer connection on one end and a connection for tubing on an opposite end and also includes a bisected lever arm with an opening for accommodating the tubing at one end and an occluding mechanism at an opposite end, the occluding mechanism including left and right bearing surfaces and left and right axles mounted eccentrically on the left and right bearing surfaces. The transfer system also includes an upper housing and a lower housing configured for assembly around the tubing and a portion of the connector, and wherein the left and right bearing surfaces mount in mounting surfaces of the upper and lower housings, and a bushing for mounting on the left and right axles, wherein the tubing is occluded when the lever arm is in a first position and the bushing squeezes and occludes the tubing and wherein the tubing is opened when the lever arm is in a second position and the bearing surfaces and the bushing are retracted, allowing the tubing to open.

Another embodiment is a transfer system. The transfer system includes a connector having a luer connection on one end and a tubing connection on an opposite end, a clamp front including an upper portion and a lower portion, the upper portion including a longitudinal opening for tubing and a transverse rib for occluding the tubing, the lower portion including at least one deformable tab and a transverse opening, and also includes a clamp back including an upper portion and a lower portion, the upper portion including a longitudinal opening for tubing and a catch, the lower portion including a left half and a right half, each half including a first smaller transverse opening and a second larger transverse opening, wherein a portion of the clamp front fits between the left half and the right half. The transfer system includes a left horn ring and a right horn ring for mounting in the lower portion transverse openings of the clamp front and the larger transverse openings of the clamp back, and also includes an occluder for mounting in the smaller transverse openings of the clamp back lower portion, wherein the tubing is occluded when the transverse rib is in a first position and the transverse rib and the transverse occluder press against the tubing to occlude the tubing, and wherein the tubing is opened when the transverse rib is in a second position and the transverse rib does not press against the tubing.

Another embodiment is a transfer system. The transfer system includes a connector having a luer connection on one end and a connection for tubing on an opposite end, an upper housing and a lower housing configured for assembly around the tubing and a portion of the connector, the upper and lower housings captured by the connector, and also includes at least one occluding pin captured within the housing. The transfer system also include a mechanism for moving the at least one occluding pin into and out of bearing contact with the tubing for occluding the tubing, wherein the mechanism has a first retracted position for occluding the tubing and a second extended position for not occluding the tubing, and wherein the retracted and extended positions are distinct from one another and are visible to a user of the transfer system.

In an embodiment, the transfer system is adapted for peritoneal dialysis and includes an output device for indicating an end of a dwell time or a time remaining of the dwell time.

In an embodiment, the transfer system is adapted for remote control of peritoneal dialysis and includes a microcontroller and a wireless device for communicating with a peritoneal dialysis machine.

In an embodiment, the transfer system includes an audio output device or a video output device for communicating with a patient or a caregiver.

In an embodiment, the transfer system is adapted for peritoneal dialysis and includes an output device for communicating with a patient and an input device for sending a signal to a controller of a peritoneal dialysis machine.

In an embodiment, the transfer system includes a remotely-operated output device for communicating with a patient.

Additional features and advantages are described herein, and will be apparent from the following Detailed Description and the figures.

BRIEF DESCRIPTION OF THE FIGURES

FIGS. 5-7 depict a first embodiment of a transfer set device;

DETAILED DESCRIPTION

Patients for whom peritoneal dialysis is prescribed appreciate ease of use of the sometimes-bulky equipment necessary for infusion and return of dialysis fluid. This applies especially to devices that connect the peritoneal dialysis machine to the catheter or other patient access device that has been implanted in the patient. Such devices or connectors are of course required, but they present an opportunity for infection if handled improperly. They may present an obstacle to a patient if they are not convenient to connect and to use. They also present an impediment to starting a dialysis or other therapy session if it is not easy to tell whether the transfer set or tubing is in an open or an occluded position. The transfer sets disclosed herein are useful in overcoming these obstacles.

Figure 1:
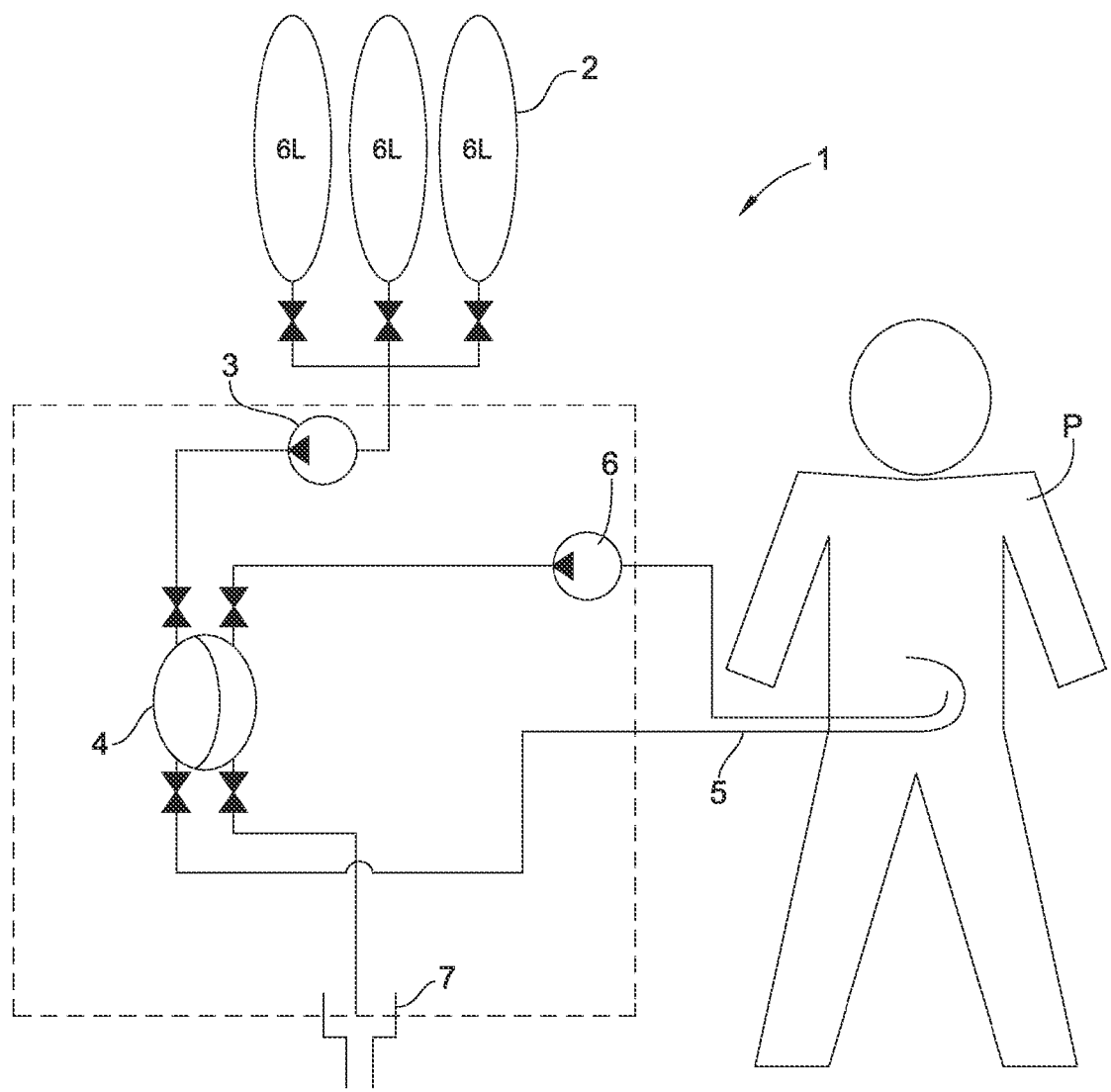
FIG. 1 is a prior art peritoneal dialysis system.

Dialysis therapy is typically conducted with a peritoneal dialysis machine, such as the machine depicted in FIG. 1. One suitable peritoneal dialysis machine is the HomeChoice® peritoneal dialysis machine from Baxter International, Deerfield, Ill., U.S.A. A patient P is connected to a dialysis machine 1, shown within the dashed lines, with a patient access device 5, such as an implanted catheter as shown. The catheter may be a single lumen or double lumen catheter, or another type of access device may be used. A plurality of containers 2 of dialysis solution is connected to the dialysis machine, as shown, through valves or other connectors. A pump 3 is used to transport dialysis fluid from the containers 2, one at a time, through a balance chamber 4 to the peritoneal cavity of the patient P through the access device. After the peritoneal dialysis solution has remained within the patient for the desired dwell time, the same pump 3 or another pump 6 may be used to pump the spent dialysis solution through the balance chamber 4 and then to a drain 7.

Figure 2:
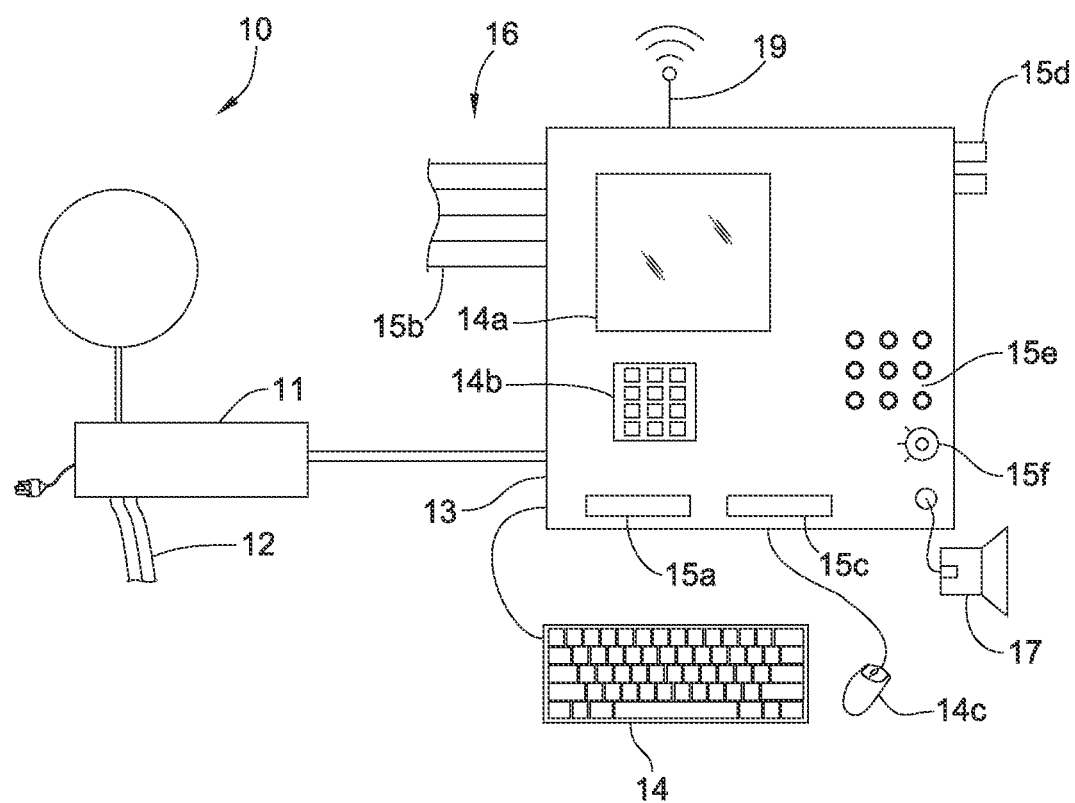
FIG. 2 is a control system for a peritoneal dialysis system.

In embodiments discussed herein, a dialysis machine 1 may be used with a dialysis control system 10 as depicted in FIG. 2. Dialysis control system 10 includes an operating portion, such as the peritoneal dialysis machine depicted in FIG. 1, including fluid lines 12 for connection to a patient access device, such as a catheter (not shown). The operating section 11 performs dialysis for the patient under the supervision of a control unit 13. Control unit 13 in one embodiment has at least an input keypad 14, control panel 14a, which may be a touch screen, input number pad 14b, and mouse 14c. The control unit will also include input drive 15a, which may be suitable for a floppy drive or for a CD drive. The computer in this embodiment is configured with a port for Internet access 15b, as well as additional inputs and outputs, including ports 16. The additional input ports may be any combination of serial ports, such as USB ports, or parallel ports.

In some embodiments, the control unit will be adapted to receive commands from a remote control unit, and will include an IR receiver 15c for a hand-held remote. Inputs/outputs may include an optical input or output 15d and other digital or analog inputs. Control portion 15e includes a series of controls knobs or switches for operating the dialysis machine. A speaker output 17 can alert the patient or a caregiver if there is an emergency or other malfunction of the dialysis machine. There is also a visual alarm 15f for alerting the patient or caregiver. The control section includes an antenna 19 for receiving remote commands or information. The antenna may be used for communication with a wireless device for the patient, as discussed below. The antenna may also be used for wireless (WiFi) internet access or may be used for remote, but closer, commands.

Figure 3:
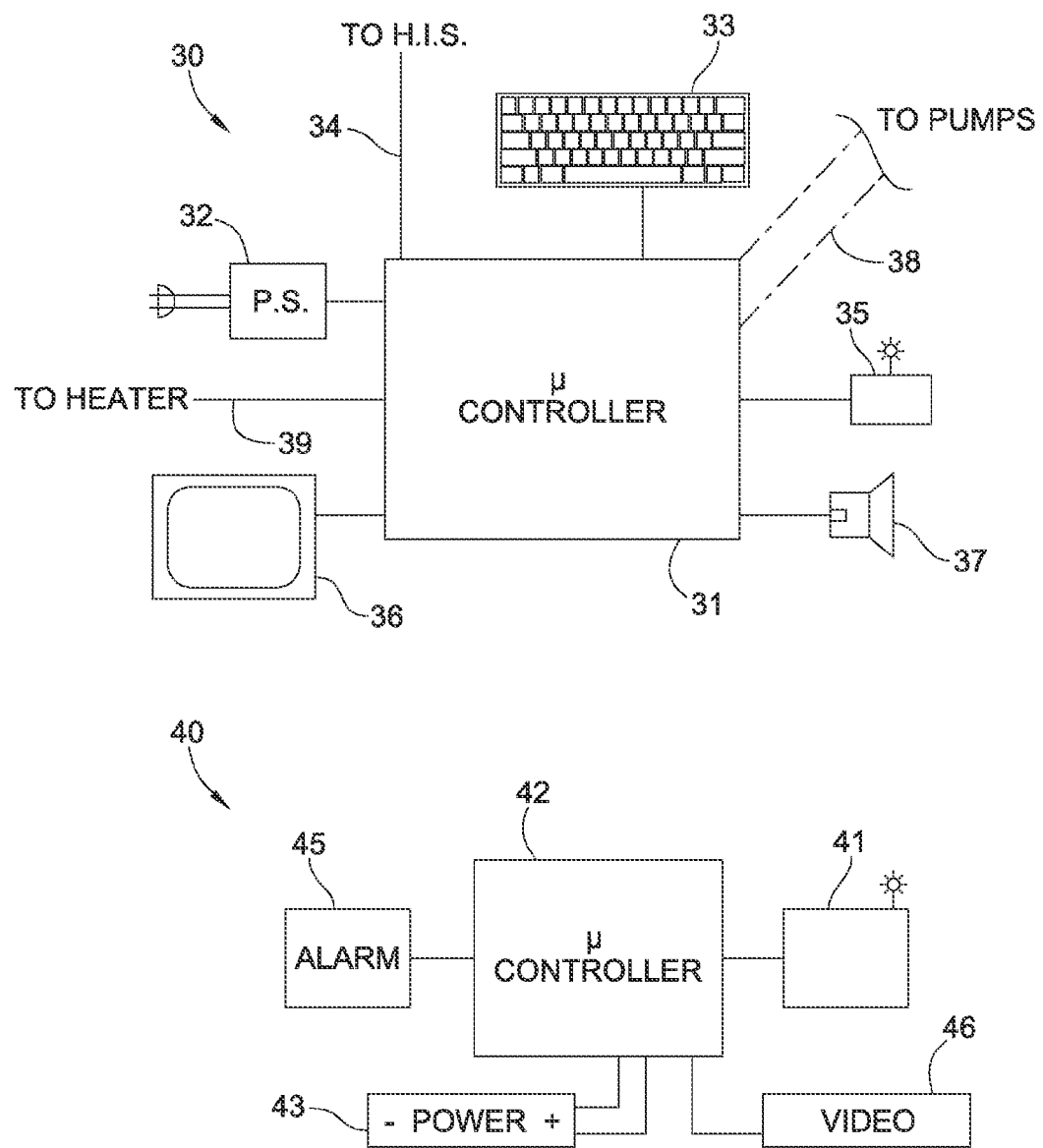
FIG. 3 is schematic view of a more detailed control system for a peritoneal dialysis system.

FIG. 3 depicts a closer view of the control portions 30 of the dialysis machine 10. Machine control portion 30 is in communication with a "smart" patient control portion 40. As seen in FIG. 3, the communication is wireless, for convenience and mobility of patients, such as mobile CAPD patients. However, those with skill in the art will recognize that a wire harness or cable could also connect the two portions. Dialysis machine control portion 30 includes a supervisory microcontroller 31, which receives power from a power supply 32. The microcontroller receives inputs from at least a keypad 33, and may also receive data and commands from a wired connection 34, such as from a clinic or hospital information system. Inputs may also be received from the patient via wireless connection and radio 35. The microcontroller has outputs to a video monitor 36, a speaker 37, as well as controls to the dialysate pumps 38 and a heater 39 for the dialysate. The machine control system includes at least one memory as a part of the microcontroller 31 or accessible by the microcontroller 31.

The patient control portion 40, as noted above, is not attached to the dialysis machine, enabling a mobile patient to move about without a wire harness or other connecting cable. Of course, other embodiments may include a cable, infrared (IR) or RF communications instead of the radio described herein. The patient control portion includes a separate microcontroller 42 and power supply 43, such as a battery 42. The controller 42 receives input from the radio 41, with outputs through the radio and to an audio alarm or speaker 45 and a small video monitor 46. In some embodiments, the patient control portion may also include switches or other electromechanical inputs for signaling the microcontroller 42 or for controlling the operation of the patient control portion 40.

The signal processing circuitry and radio 41 or wireless receiver/transmitter are small and compact, and are easily placed on the patient at the access site, such as in a "smart" module or connector. One radio that works is a wireless module in accord with ZigBee/IEEE 805.15.4. This is a standard for a very low power radio system with a very limited range, about 10-20 feet. Modules made in accordance with this standard may be purchased from Maxstream, Inc., Lindon, Utah, U.S.A., Helicomm, Inc., Carlsbad, Calif., U.S.A., and ANT, Cochrane, Alberta, Canada. The module is very small, and may be about 2 cm square (about 1 inch square), and about 3 mm thick (⅛ inch). The patient control portion 40, as noted, is intended for close proximity, within range of the ZigBee module, of about 10-20 feet, of the dialysis machine. Thus, the local portion or signal module is conveniently small and unobtrusive for the patient, but fully capable of communication and control with the machine control portion 30.

The patient may use the patient control portion or may simply use the dialysis machine, such as the embodiment depicted in FIG. 2. In one embodiment that does not use a smart module, shown in FIG. 4a, the patient P is connected to the dialysis machine through patient line 18, through transfer set 50, and a catheter serving as a peritoneal access device 47. The transfer set 50 is connected via luer connectors or other suitable connectors. The transfer set, into which the patient control device can be integrated, includes a length of tubing for connecting to the patient access device and for connecting to the patient line. Those who have skill in the art will recognize that patient transfer sets vary in regards to the connecters used. In this embodiment, the patient access device 47 is a double-lumen catheter and the patient line 18 includes two lengths of tubing. In another embodiment not shown herein, the transfer set 50 may include the circuitry depicted in FIG. 3 for remote communication with the peritoneal dialysis machine.

Figure 4A:
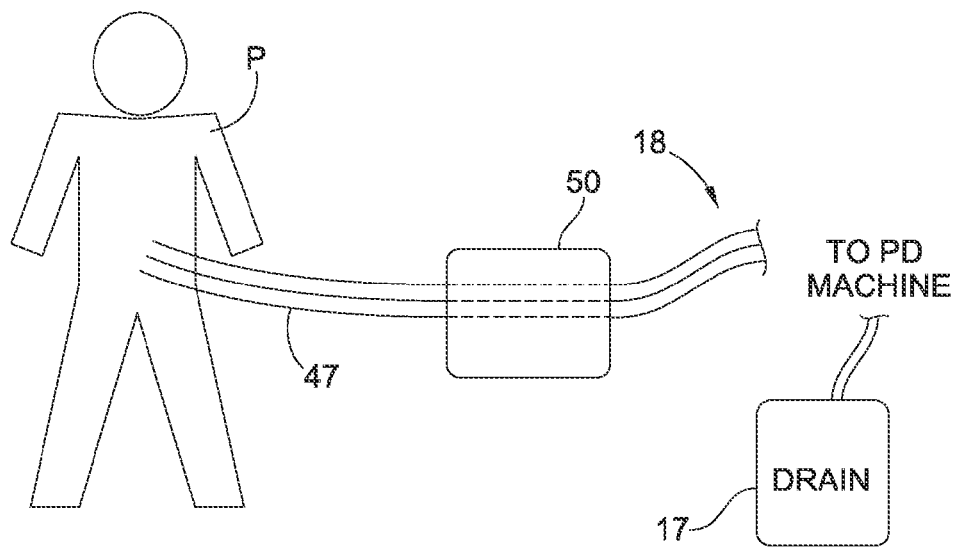
FIGS. 4A and 4B are embodiments of dialysis systems for use with double-lumen or single-lumen transfer sets.
Figure 4B:
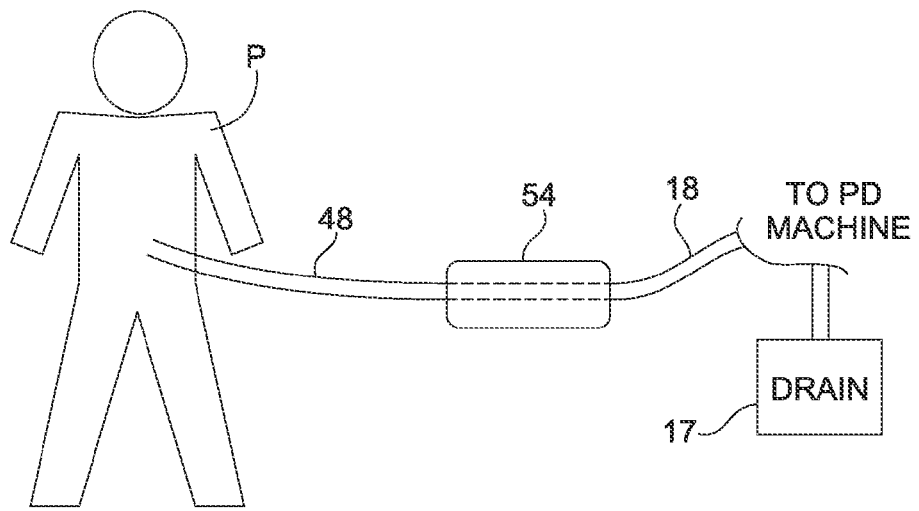

Another embodiment of the patient control device and its application is depicted in FIG. 4B. Patient P is connected to the dialysis machine through a single-lumen patient line 18, transfer set 54, and a single-lumen catheter 48 serving as a patient access device. Patient control device 54 is connected via luer connectors or other suitable connectors.

In another embodiment not shown herein, the transfer set 50 or 54 may include the circuitry depicted in FIG. 3 for remote communication with the peritoneal dialysis machine. As disclosed in co-pending U.S. Prov. Appl. 61/050,144, entitled "Optimizing Therapy Outcomes for Peritoneal Dialysis," filed on May 2, 2008, which is hereby incorporated by reference in its entirety and is relied on, the patient control device may include a small video output and a lamp. An audio alarm may be used to signal the patient to begin or end a therapy session. The video output is suitable for displaying a time remaining on the dialysis session, e.g., a dwell time or a remaining portion of a dwell time. The lamp may be used to signal the patient to start therapy or that therapy is complete. The patient control device may also include switches, suitable for allowing the patient to respond to queries from the microcontroller 42. The switches for example, may be "yes" and "no" switches that are suitable for responding to queries from the controller, such as "shall we start the dialysis session?" or "please enter a start time for the dialysis session."

Axial Pin Transfer Device

Figure 5:
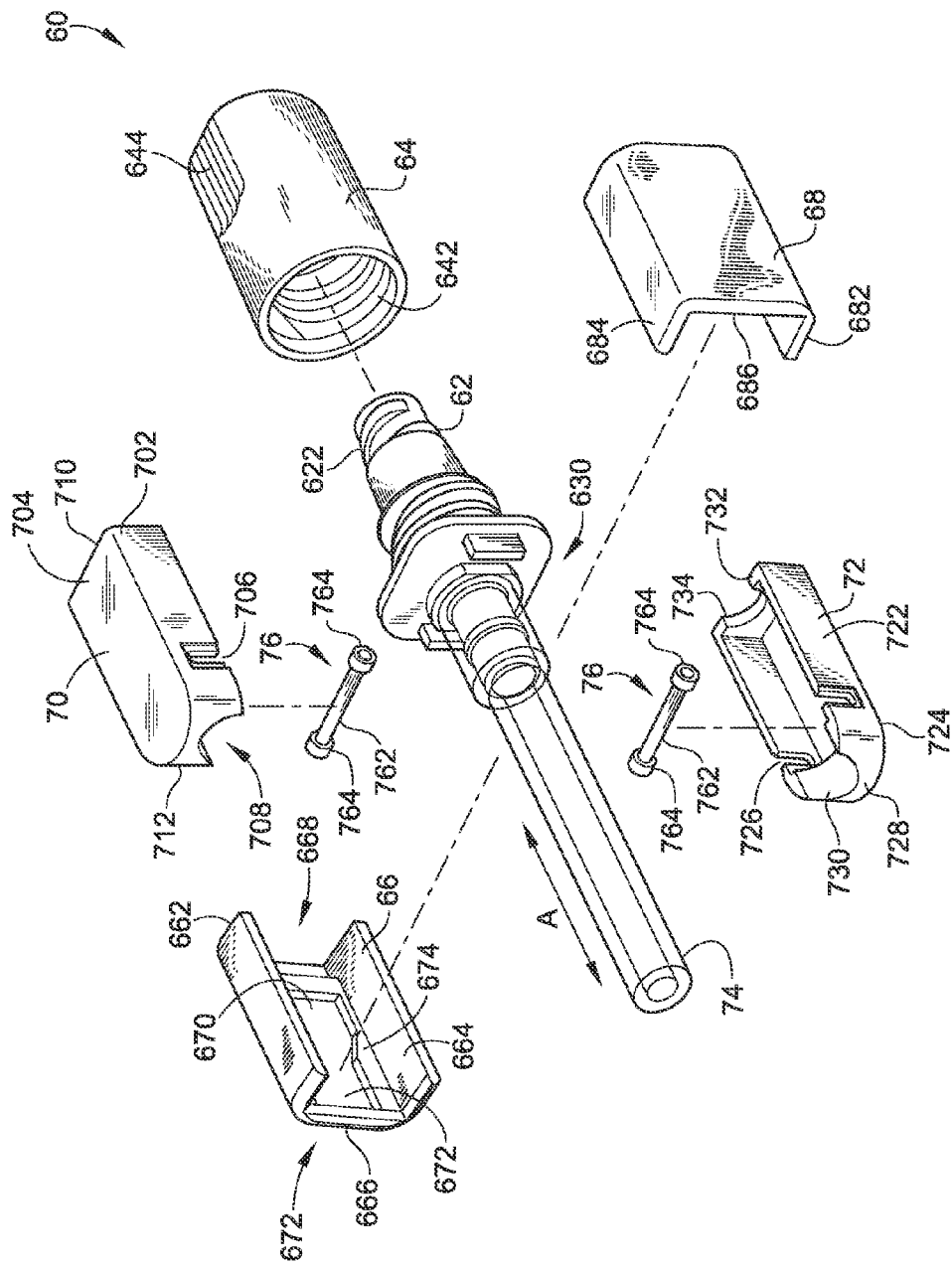

A first embodiment of a transfer device or transfer set 60 is depicted in FIGS. 5-7. This transfer set is an integrated clamp and connector in that it includes connectors and a clamp for allowing and preventing flow of the fluid to and from the patient. This transfer set is known informally as an axial pin transfer set because it functions by movement of two pins across the longitudinal axis of the tubing. Transfer set 60 includes a connector 62, a cap 64, left and right retractors 66, 68, upper and lower housings 70, 72, and a length of tubing 74. The tubing may be silicone tubing or the tubing may be made of another material. The tubing, which is flexible, has a longitudinal axis A, as shown in FIG. 5. In one embodiment, cap 64 includes female mating threads 642 and gripping portion 644.

Connector 62 in this embodiment is a connector with luer portion 622 on one end and a straight tubing connector portion 630 on an opposite end. The tubing connector portion 630 may include retaining barbs 628 which are molded as part of the connector and over which tubing 74 may be pulled to insure the tubing remains in place. As shown best in FIG. 7, connector 62 also includes radial tubing stop 626 and a radial undercut 632 behind tubing stop 626. Undercut 632 provides a gap for retaining end portions of the upper and lower housings 70, 72. In this embodiment, luer connector portion 622 is a male luer thread, suitable for threaded engagement with female luer protective cap 64, which is also known as a mini-cap. Other embodiments may use other connectors, such as a female-threaded luer connector with a male-threaded luer cap, or entirely different connectors, as suitable and as desired.

Upper and lower housings 70, 72 are placed around the tubing 74 and connector 62. The upper and lower housings are captured by the undercut 632. The upper and lower housings each have a semi-circular opening suitable for capture by the undercut, such as semi-circular opening 734 depicted on lower housing 72. The upper housing has a side flange 702 and a tombstone-shaped top surface 704, that is, top surface 704 is flat on the end 710 nearer tube stop 626 and is rounded on the end 712 away from connector 62. Side flange 702 includes a semi-circular opening 708 on one end and a second semi-circular opening (not shown) on the other end, to allow passage of the tubing through the flange. In addition, flange 702 includes two slots 706 perpendicular to top surface 704.

Lower housing 72 includes a side flange 722 and a bottom surface 724. Side flange 722 includes a rounded end 728 with semi-circular opening 730 and a flat end 732 with a semi-circular opening 734, the semi-circular openings allowing passage of the tubing 74. Flange 722 also includes two slots 726 perpendicular to bottom surface 724. Slots 706, 726 in the top and bottom housings 70, 72 allow up-and-down movement of pins 76 within the slots. Pins 76 include a cylindrical pin 762 and roller bearings 764. In one embodiment, the roller bearings are dimensioned so that while they are movable up and down in slots 706, 726, the bearings 764 themselves do not have sufficient clearance to rotate, instead allowing pin 762 some limited freedom of rotation.

The axial pin transfer set 60 also includes left and right retractor housings 66, 68. When assembling the transfer set, upper and lower housings 70, 72 fit within the left and right retractor housings 66, 68. The upper and lower housings 70, 72 are assembled about the tube stop 626 and then ultrasonically welded in place by their flanges or otherwise affixed, such as by solvent bonding, adhesive bonding, or other reliable technique. The left and right retractor housings 66, 68 are then assembled by their flanges about the assembled upper and lower housings. The left and right retractor housings are held together by ultrasonically welding them in place, or by one of the techniques described above for the upper and lower housings. Alternatively, the upper and lower housings, or the left and right housings, may be assembled using mating snap fits, external clamps, or any other suitable and reliable technique.

Left retractor housing 66 includes a web 666 and flanges 662, 664. Right retractor housing 68 includes a central web 686 and flanges 682, 684. The inner surface of web 666 includes a cam surface 668 with a wide portion 670, a narrow portion 672, and angled transition portion 674 between the wide and narrow portions 670, 672. The cam surface 668 is formed by molding the retractor housing 66 with an inset cam surface, or by machining the inner surface to remove sufficient material to accommodate the bearings 764 or the pin 762 itself if the embodiment in question does not use bearings.

Figure 8:
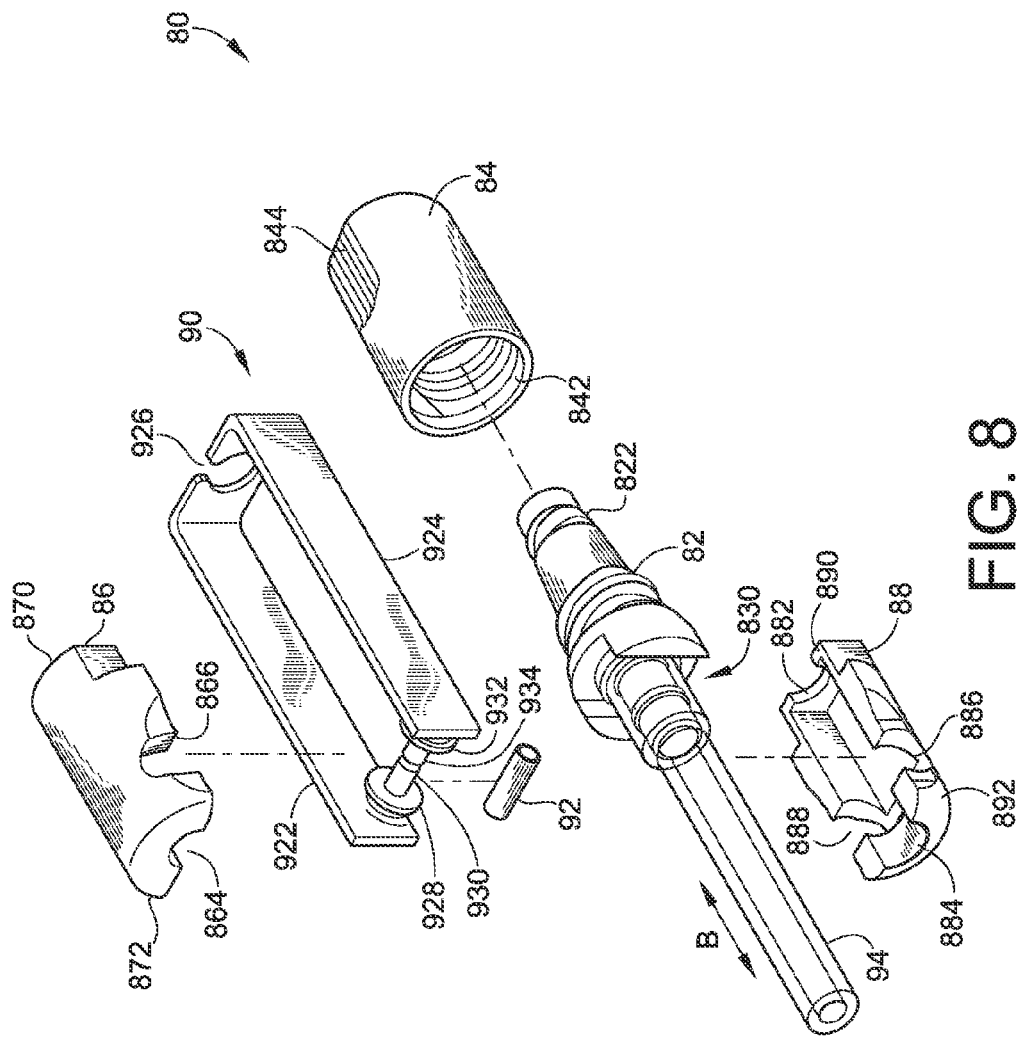
FIGS. 8-9 depict a second embodiment of a transfer set device.
Figure 9:
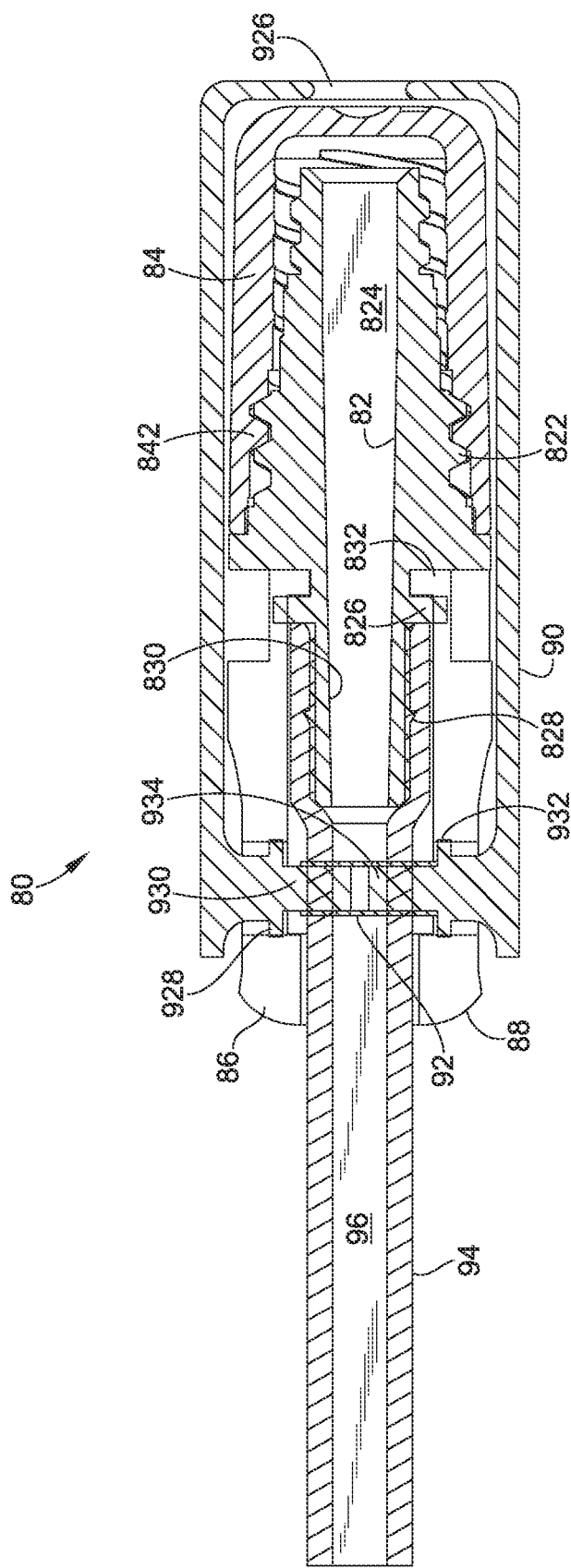
Figure 10:
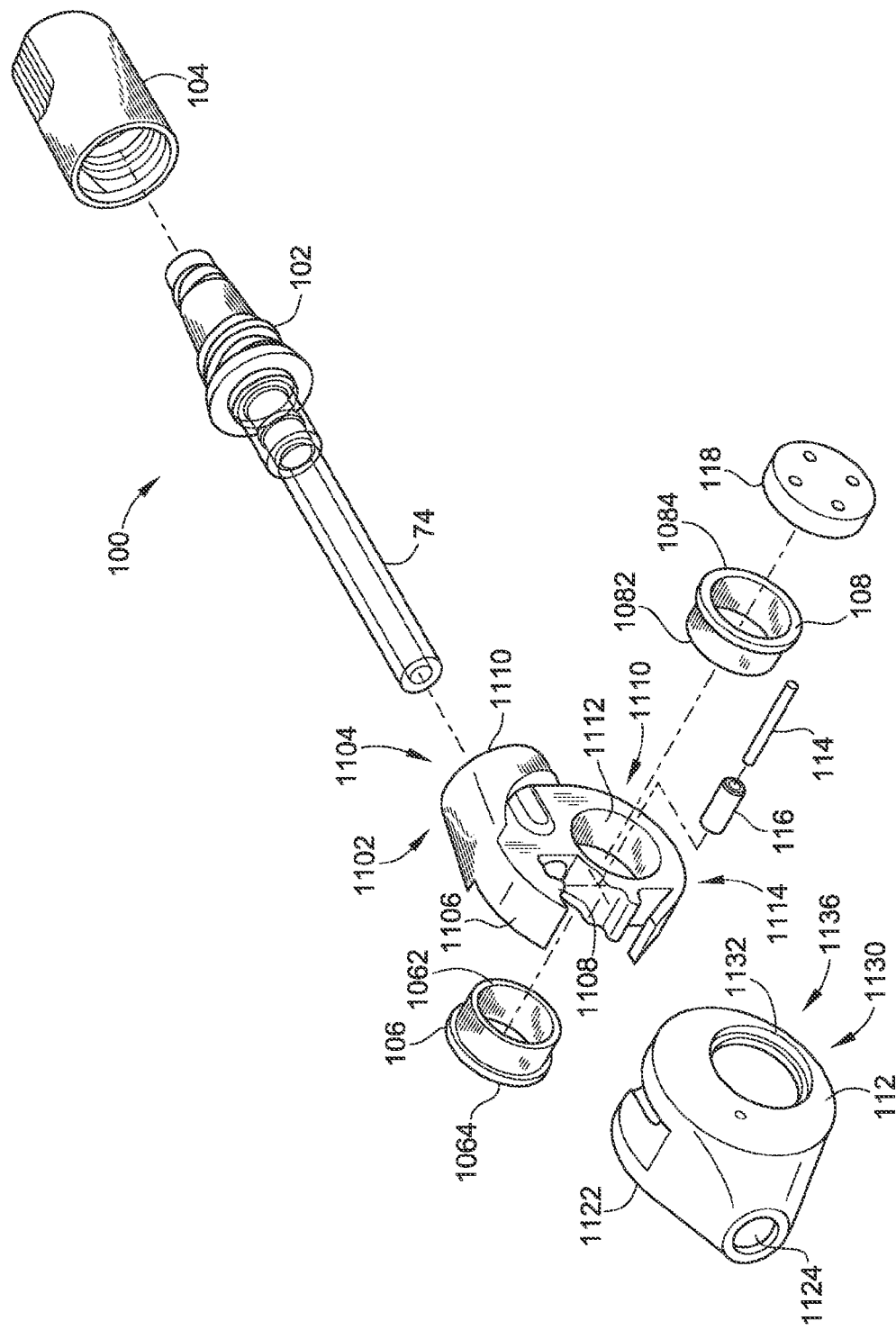
FIGS. 10-13 depict a third embodiment of a transfer set device.

The transfer set operates by first connecting the transfer set to a patient connector, preferably with the tubing, and to a disposable set of a peritoneal dialysis treatment machine with the luer connector, as shown in FIGS. 4A and 4B. In some embodiments, there may be a single connector, as shown in FIGS. 7-9 or there may be a double connector for use with a dual-lumen catheter and a peritoneal dialysis system with inlet and drain lines.

In this embodiment, and in the configuration shown in FIG. 6, the retractor housings 66, 68 are slid all the way to the right, such that they abut the widest portion of connector 62. As seen from FIG. 5, this means that the pins 76 are captured by the narrow portion 672 of cam surface 668 of the retractor housings. When the pins 76 are in this position, they force the inner portions of the tubing to connect, thus occluding the tubing, as shown in FIG. 6, and preventing flow of fluid to or from the patient. When flow is desired, the retractor housings are slid to the left, so that the wide portions 670 engage the pins. The natural force of the tubing then pushes the pins apart, the tubing is no longer occluded, and flow may begin when the patient activates the dialysis machine. Flow will then proceed through connector lumen 624 and tubing lumen 78. Alternatively, flow may begin by gravity flow, induced by the pressure difference between a source of fluid and the drain, for example, the height difference between the peritoneum of the patient and the drain bag.

The axial pin connector is simple and easy to operate. It may be used for an extended period of time, for example, overnight, while allowing for numerous stops and starts of flow. The patient or a caregiver can tell at a glance whether the connector is in an "open" or a "closed" state, by glancing at the retractors—when the retractors are close to the luer or other connector, that is, closed up, the transfer set is closed. When the retractor housings are extended and are away from the connector, the connector is open and drains and fills are possible. In addition, in this embodiment, bearings 764 are visible from the outside. If the bearings 764 of pins 76 are near each other, as in FIG. 7, the tubing is occluded; if they are separated, the tubing is not occluded and flow is possible. Other embodiments may include different configurations of the cam surface, e.g., more gently curved surfaces.

Lever Arm Transfer Device

A second embodiment of a transfer device is a lever arm transfer device shown in FIGS. 8-9. As discussed above for the axial pin device, there are many embodiments of the lever arm transfer device, including a two-tube version which includes two connectors and one or two lever arms to open or occlude two tubes at once. FIG. 8 depicts an exploded view of lever arm transfer device 80, while FIG. 9 depicts the device 80 with the lever arms in a retracted position, indicating that flow is occluded. Lever arm transfer device 80 includes a connector 82 with a male luer connection 822 and a tubing connection 830 for attachment of flexible, resilient tubing 94. The tubing connector portion 830 may include retaining barbs 828 which are molded as part of the connector and over which tubing 94 may be pulled to insure the tubing remains in place. In this embodiment, connector 82 also includes radial tubing stop 826 and a radial undercut 832 behind tubing stop 826. Tubing 94 has a longitudinal axis B along the length of the tubing. Transfer device 80 also includes a cap 84 with female threads 842 and a gripping surface 844. The cap protects the sterility and integrity of connection 822 and is removed in order to connect to a dialysis machine (not shown). Transfer device 80 will typically be connected to a patient with tubing 94 and to a dialysis machine with connector 82.

Lever arm transfer device 80 also includes a bisected lever arm 90, a bushing 92 and upper and lower housings 86, 88. Upper and lower housings 86, 88 are each in the general shape of a truncated half-tube and are configured to fit over connector 82 and tubing 94, capturing the tubing stop 826, as shown in FIG. 9. The upper and lower housings are held together by solvent or adhesive bonding, ultrasonically welding, or other suitable technique as described above for the axial pin design. Lower housing 88 includes first and second semicircular end openings 882, 884 to allow axial passage of tubing 94, and also includes left and right semicircular openings 886, 888. End opening 882 is formed in the flat end distal portion 890, distal portion 890 being the portion of the lower housing away from the patient. Rounded end proximal portion 892, the portion of the lower housing closer to the patient, is somewhat wider than distal portion 890. The upper housing 86 is configured in a similar manner, with a narrower, flat end 870 and a wider, rounded end 872 and apertures or cut-aways similar to those of the lower housing 88. Only the right side opening 866 and proximal opening 864 are visible in FIG. 8 since the far side of the upper housing cannot be seen.

Lever arm 90 is configured as shown in FIG. 8, and is intended for movement and rotation about left and right bearing surfaces 928, 932. Lever arm 90 includes left and right arm portions 922, 924, and terminal opening 926, which is roughly circular in shape. The configuration of the opening 926 allows the user or the patient to squeeze tubing 94 into opening 926 in either the occluded or the open position. Of course, this configuration also allows for removal of the tubing when the user desires to switch from one position to the other. Left and right axles 930, 934 are mounted perpendicularly to and eccentrically upon bearing surfaces 928, 932. Axles 930, 934 are configured to mount bushing 92 which is used to occlude tubing 94.

FIG. 9 depicts the lever arm transfer device 80 in a closed state, with the lever arm 90 rotated to the right, as shown, and the tube 94 occluded by bushing 92. The lever arm transfer device is operated by rotating the lever arm 180° from the closed position to the open position. As the arm rotates, the bearing surfaces 928, 932 rotate within side openings 888, 886 of the lower housing 88 and side openings of the upper housing 86, only one opening 866 depicted. The bearing surfaces 928, 932 rotate on centers, as do the arms 922, 924, centered on the bearing surfaces. However, the axles 930, 934, and the bushing 92 rotate eccentrically, so that in one position, when the lever arm is to the right, as shown in FIG. 9, the bushing 92 impinges on the tubing, squeezing and occluding the tubing. When rotated 180°, the bushing is moved out of contact with the tubing, allowing the tubing to expand and assume its natural, round shape, thus opening and allowing flow through lumen 96 of tubing 94 and through lumen 824 of connector 82.

It will be understood by those having skill in the art that the axles may be positioned for other opening and occluding movements of the lever arm, e.g., 90° or other desired angle, to occlude or to open the tubing. Using a 180° angle, the lever arm will be retracted, as shown in FIG. 9 when the tubing is occluded, and will be extended along the length of the tubing (extended view not shown) when rotated 180° to open the tubing and allow flow of fluid to and from the patient. The user can easily tell whether transfer set 80 is occluded or open by noting whether lever arm 90 is retracted and near connector 82 or extended and away from connector 82.

Cam Clamp Transfer Device

A third embodiment of a transfer device is depicted in FIGS. 10-13. This is the "cam clamp" transfer device, named because of the shape of the components. As seen in the exploded view of FIG. 10, this transfer device 100 includes a tubing connector 102, a protective cap 104, and a length of tubing 74. Components also include a clamp front 110, a clamp back 112, and left and right horn rings 106, 108 for mounting in the clamp back 112. There is also a support rod 114 and an occluding bushing 116 for mounting in the clamp back 112. A horn or alarm 118 mounts within the horn rings. The cam clamp device is typically used to connect to a patient via tubing 74 and to a dialysis or other machine with connector 102.

Figure 11:
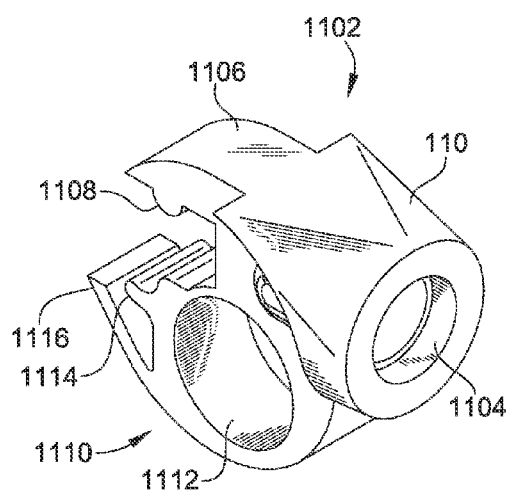

A closer, perspective view of the clamp front 110 and its component parts is depicted in FIG. 11. Clamp front 110 includes an upper portion 1102 and a lower portion 1110. Upper portion 1102 includes an opening 1104 for tubing 74, the opening intended to face the connector 102. Upper portion 1102 also includes an extension 1106 with a transverse rib 1108. The rib 1108 is transverse to a longitudinal axis of the tubing 74. The lower portion 1110 includes a transverse opening 1112 and, in this embodiment, stop tab 1114 and release tab 1116. Horn rings 106, 108 mount on opposite sides of openings 1136, 1138 in the clamp back and extend through to opening 1112 in the clamp front. Horn rings 106, 108 include central inner cylindrical portions 1062, 1082 and outer flanges 1064, 1084, which limit the intrusion of the rings into the openings 1136, 1138. Clamp front 110 is flexible and may be made of an elastomer, such as silicone rubber, butyl, nitrile, or other medically acceptable elastomeric or plastic material.

Figure 12:
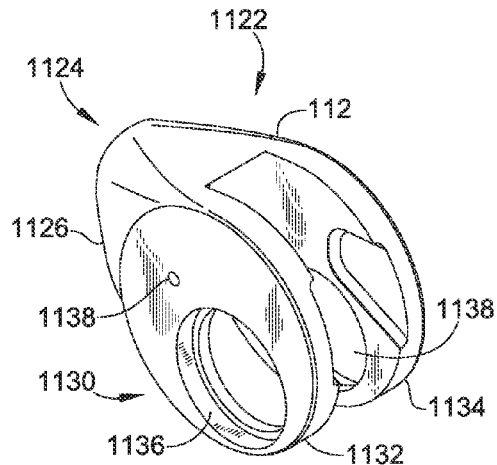

An isometric view of clamp back 112 is depicted in FIG. 12. Clamp back 112 is intended to be a stiffer material, and may be made of metal, or preferably, a medically acceptable, stiff plastic or elastomeric material. Clamp back 112 includes an upper portion 1122 and a lower portion 1130. Upper portion 1122 includes an opening 1124 suitable for passage of tubing 74 and also includes a catch 1126. The transfer device is assembled by placing the lower portion 1110 of the front clamp 110 between the halves 1132, 1134 of the lower portion 1130 of the back clamp, and by placing the extension 1106 and transverse rib 1108 within the upper portion 1122 of the back clamp. Horn rings 106, 108 extend through openings 1136, 1138 in clamp back 112 and then into opening 1112 of the clamp front 110. The flanges 1064, 1084 of the horn rings allow rotation of the clamp front with respect to the clamp back for occlusion of the tubing 74 between rib 1108 and bushing 116.

Figure 13:
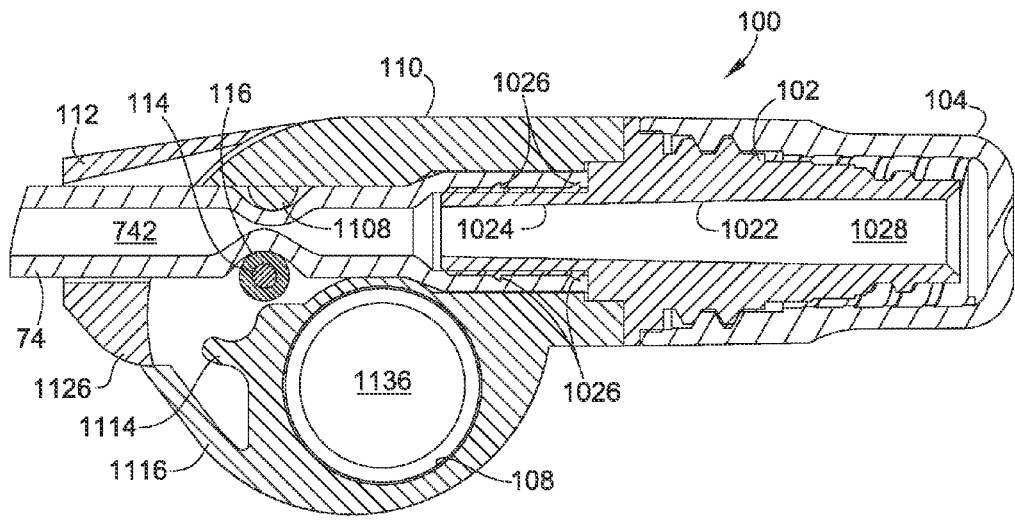

As shown in FIG. 13, connector 102 includes a luer-type connector portion 1022 and a tubing-type connector 1024. Tubing 74 may be retained on the tubing connector 1024 by barbs 1026. This embodiment is actuated by a user pushing downwardly on extension 1106 of the front clamp 110, causing the clamp front 110 to rotate counter-clockwise with respect to the clamp back 112 and causing extension 1106 to move forward and be caught by catch 1126 of the back clamp. The catch 1126 should be suitable for gripping extension 1106 of the front clamp, causing transverse rib 1108 to press against tubing 74 from the top while the rod 114 and bushing 116 restrain the movement of the tubing from below. Stop tab 1114 prevents further rotation or movement of front clamp 110 when rotation causes stop tab 1114 to bear against bushing 116.

The pressure of the transverse rib against the tubing thus occludes the tubing and prevents flow of fluid within the tubing. When fluid flow is desired, the user presses clockwise or upwardly on release tab 1116, releasing the extension 1106 from catch 1126, and removing the occluding force from the tubing. Fluid may then flow within lumen 742 of the tubing and within lumen 1028 of connector 102. The user or a caregiver is easily able to determine whether the transfer device is in an occluded or closed state, or in an open state. If the extension 1106 is down and caught on the catch, the device is occluded; if the extension has been released, the device has been opened for fluid flow.

A horn or alarm 118 is optionally placed within the horn rings 106, 108. In this embodiment, the horn or alarm is configured in the manner depicted in FIG. 3 above, but without a video output. Thus, the horn includes an alarm 45, which may have an audio output or may have a buzzer output. The controller 42 of the alarm may be programmed to sound after a recommended or optimized dwell time, for example, from 1 to 8 hours of dwell for a peritoneal dialysis solution.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A patient fluid transfer device comprising:
   a connector including a tube receiving end;
   a clamp front abutting the connector and including
      a longitudinal tube receiving opening,
      a transverse opening,
      an extension having an occluding rib, and
      a deformable tab;
   a clamp back including
      a longitudinal tube receiving opening,
      a first half defining a first half transverse opening,
      a second half defining a second half transverse opening,
      a rod held between the first half and the second half, and
      a catch,
   wherein the extension and the deformable tab of the clamp front are fitted between the first and second halves of the clamp back such that the transverse opening of the clamp front is aligned with the first half transverse opening and the second half transverse opening; and
   first and second rings fitted into the first half transverse opening and the second half transverse opening, respectively, forming a pivot about which the clamp front can rotate with respect to the clamp back (i) in a first direction such that an external tube is occluded between the occluding rib and the rod and the deformable tab is caught by the catch and (ii) in a second direction when the deformable tab is deformed so that the deformable tab is not caught by the catch, allowing the occluding rib to move away from the rod for opening the external tube.

2. The patient fluid transfer device of claim 1, which includes a bushing fitted around the support rod, the external tube occluded between the occluding rib and the bushing.

3. The patient fluid transfer device of claim 1, wherein the clamp front is made of a material that is flexible relative to a material of the clamp back.

4. The patient fluid transfer device of claim 1, wherein the first and second rings include an inner pivot portion and an outer flange for fitting to the first and second halves, respectively.

5. The patient fluid transfer device of claim 1, wherein the longitudinal tube receiving openings of the clamp front and the clamp back are at least substantially aligned when the external tube is occluded.

6. The patient fluid transfer device of claim 1, wherein the extension of the clamp front is configured to be pressed to rotate the clamp front in the first direction such that the external tube is occluded between the occluding rib and the rod and the deformable tab is caught by the catch.

7. The patient fluid transfer device of claim 1, wherein the deformable tab of the clamp front is configured to be pressed to rotate the clamp front in the second direction such that the tab is not caught by the catch, allowing the occluding rib to move away from the rod for opening the external tube.

8. The patient fluid transfer device of claim 1, wherein the extension and the deformable tab of the clamp front extend circumferentially towards each other, leaving a gap between the extension and the deformable tab.

9. The patient fluid transfer device of claim 8, which is configured such that the external tube extends within the gap.

10. The patient fluid transfer device of claim 1, wherein the deformable tab is a first tab, and wherein clamp front includes a stop tab that abuts the rod when the clamp front has rotated in the second direction to an end-of-travel position with respect to the clamp back.

11. The patient fluid transfer device of claim 1, wherein the tube receiving end of the connector includes a hose barb.

12. The patient fluid transfer device of claim 1, wherein an end of the connector opposing the tube receiving end includes a luer connection.

13. The patient fluid transfer device transfer system of claim 1, which includes an alarming mechanism having an output for informing a patient.

14. A patient fluid transfer device comprising:
a clamp front including
a longitudinal tube receiving opening,
a transverse opening,
an extension having an occluding end, and
a deformable tab; and
a clamp back including
a longitudinal tube receiving opening,
a transverse opening,
a transverse occluding member located adjacent the transverse opening, and
a catch,
wherein the transverse opening of the clamp front is aligned along a same transverse line with the transverse opening of the clamp back, allowing the clamp front to rotate with respect to the clamp back (i) in a first direction such that an external tube extending through the longitudinal tube receiving opening is occluded between the occluding end of the extension and the transverse occluding member and the deformable tab is caught by the catch and (ii) in a second direction when the deformable tab is deformed so that the deformable tab is not caught by the catch, allowing the occluding end of the extension to move away from the transverse occluding member for opening the external tube.

15. The patient fluid transfer device of claim 14, which includes a connector including an end receiving the external tube, the connector abutting the clamp front.

16. The patient fluid transfer device of claim 14, wherein the transverse opening of the clamp back includes a first half transverse opening defined by a first half of the clamp back and a second half transverse opening defined by a second half of the clamp back.

17. The patient fluid transfer device of claim 16, wherein the extension and the deformable tab of the clamp front are fitted between the first and second halves of the clamp back.

18. The patient fluid transfer device of claim 16, which includes first and second rings fitted into the first half transverse opening and the second half transverse opening, respectively, forming a pivot about which the clamp front can rotate with respect to the clamp back.

19. The patient fluid transfer device of claim 16, wherein the transverse occluding member is held between the first half and the second half of the clamp back.

20. A method of opening and occluding a medical fluid tube using a transfer device including (i) a clamp front having a longitudinal opening and a transverse opening, and (ii) a clamp back having a longitudinal opening and a transverse opening, the method comprising:
occluding the medical fluid tube by moving the clamp front relative to the clamp back while the transverse opening of the clamp front is aligned along a same transverse line with the transverse opening of the clamp back so that (i) a first extension of the clamp front presses against a transverse occluder of the clamp back, and (ii) a second extension of the clamp front is held by a catch of the clamp back; and
opening the medical fluid tube by pressing the second extension to release the second extension from being held by the catch.

21. A patient fluid transfer device comprising:
a connector including an end receiving an external tube;
a clamp front abutting the connector and including
a longitudinal tube receiving opening,
a transverse opening,
an extension having an occluding end, and
a deformable tab; and
a clamp back including
a longitudinal tube receiving opening,
a transverse opening,
a transverse occluding member located adjacent the transverse opening, and
a catch,
wherein the transverse opening of the clamp front is aligned with the transverse opening of the clamp back, allowing the clamp front to rotate with respect to the clamp back (i) in a first direction such that the external tube extending through the longitudinal tube receiving opening is occluded between the occluding end of the extension and the transverse occluding member and the deformable tab is caught by the catch and (ii) in a second direction when the deformable tab is deformed so that the deformable tab is not caught by the catch, allowing the occluding end of the extension to move away from the transverse occluding member for opening the external tube.

22. A patient fluid transfer device comprising:
a clamp front including
a longitudinal tube receiving opening,
a transverse opening,
an extension having an occluding end, and
a deformable tab; and
a clamp back including
a longitudinal tube receiving opening,
a transverse opening including a first half transverse opening defined by a first half of the clamp back and a second half transverse opening defined by a second half of the clamp back, the extension and the deformable tab of the clamp front fitted between the first half and the second half,
a transverse occluding member located adjacent the transverse opening, and
a catch,
wherein the transverse opening of the clamp front is aligned with the transverse opening of the clamp back, allowing the clamp front to rotate with respect to the clamp back (i) in a first direction such that an external tube extending through the longitudinal tube receiving opening is occluded between the occluding end of the extension and the transverse occluding member and the deformable tab is caught by the catch and (ii) in a second direction when the deformable tab is deformed so that the deformable tab is not caught by the catch, allowing the occluding end of the extension to move away from the transverse occluding member for opening the external tube.

23. A patient fluid transfer device comprising:
a clamp front including
a longitudinal tube receiving opening,
a transverse opening,
an extension having an occluding end, and
a deformable tab; and
a clamp back including
a longitudinal tube receiving opening, a transverse opening including a first half transverse opening defined by a first half of the clamp back and a second half transverse opening defined by a second half of the clamp back, a transverse occluding member located adjacent the transverse opening and held between the first half of the clamp back and the second half of the clamp back, and a catch, wherein the transverse opening of the clamp front is aligned with the transverse opening of the clamp back, allowing the clamp front to rotate with respect to the clamp back (i) in a first direction such that an external tube extending through the longitudinal tube receiving opening is occluded between the occluding end of the extension and the transverse occluding member and the deformable tab is caught by the catch and (ii) in a second direction when the deformable tab is deformed so that the deformable tab is not caught by the catch, allowing the occluding end of the extension to move away from the transverse occluding member for opening the external tube.

* * * * *